United States Patent [19]

Higgins et al.

[11] 4,198,990
[45] Apr. 22, 1980

[54] MOUTH MOUNTED ACCELEROMETER PACK

[75] Inventors: Aubin M. Higgins, Earlington, Ky.; James A. Fowler, Jr., Xenia; Roger W. Mercer, Fairborn, both of Ohio; Gunter H. Kroh, Manching, Fed. Rep. of Germany

[73] Assignee: The United States of America as represented by the Secretary of the Air Force, Washington, D.C.

[21] Appl. No.: 17,624

[22] Filed: Mar. 5, 1979

[51] Int. Cl.² ............................................... A61B 5/10
[52] U.S. Cl. ..................................... 128/782; 73/493; 340/573
[58] Field of Search ............... 128/782, 777, 774, 631; 73/488, 493; 340/573, 574, 576

[56] References Cited

U.S. PATENT DOCUMENTS

| | | | |
|---|---|---|---|
| 3,297,021 | 1/1967 | Davis et al. | 128/777 |
| 3,955,562 | 5/1976 | Farrar, Jr. | 128/782 |
| 3,972,038 | 7/1976 | Fletcher | 73/493 X |

*Primary Examiner*—Kyle L. Howell
*Attorney, Agent, or Firm*—Joseph E. Rusz; Richard J. Killoren

[57] ABSTRACT

An apparatus, for measuring head accelerations of a test subject, having a mouthpiece which includes metal clips for securing the mouthpiece to the upper teeth of the test subject. Three accelerometers are secured to a mounting block which is attached to the mouthpiece. The three accelerometers have their active axis located along three orthogonal axis through the mounting block. The mounting block, the accelerometers and the accelerometer leads are embedded in an electrically insulating material.

3 Claims, 6 Drawing Figures

MOUTH MOUNTED ACCELEROMETER PACK

RIGHTS OF THE GOVERNMENT

The invention described herein may be manufactured and used by or for the Government of the United States for all governmental purposes without the payment of any royalty.

BACKGROUND OF THE INVENTION

This invention relates to an apparatus for measuring head accelerations of a test subject.

Head accelerations have been measured with accelerometers mounted at various positions on the head of a test subject. With externally mounted accelerometers straps or other securing means are necessary to hold the accelerometers in place. With externally mounted accelerometers, possible interference with the instrumentation and test apparatus made it difficult and sometimes impossible to obtain accurate measurements. Externally mounted accelerometers result in the introduction of some elasticity in the mounting which allows some relative motion between the accelerometers and the head of the test subject which makes it impossible to obtain reproducible results.

BRIEF SUMMARY OF THE INVENTION

According to this invention a metal mouthpiece is cast of a dental alloy material. The mouthpiece is individually fitted to the upper teeth of each test subject and secured to the upper teeth with rigid attachments. Three accelerometers are secured to a plexiglass mounting block with their active axis along three orthogonal axis through the mounting block. The mounting, block, accelerometers and accelerometer leads are coated with a medical grade silicone elastic to provide electrical insulation for the accelerometers and the leads. The mounting block is rigidly secured to the mouthpiece. The rigid attachment of the mounting block to the mouthpiece and the rigid attachment of the mouthpiece to the upper teeth of the test subject prevents relative movement between the accelerometers and the head of the test subject thus providing reproducible results.

IN THE DRAWINGS

DETAILED DESCRIPTION OF THE INVENTION

Figure 1:
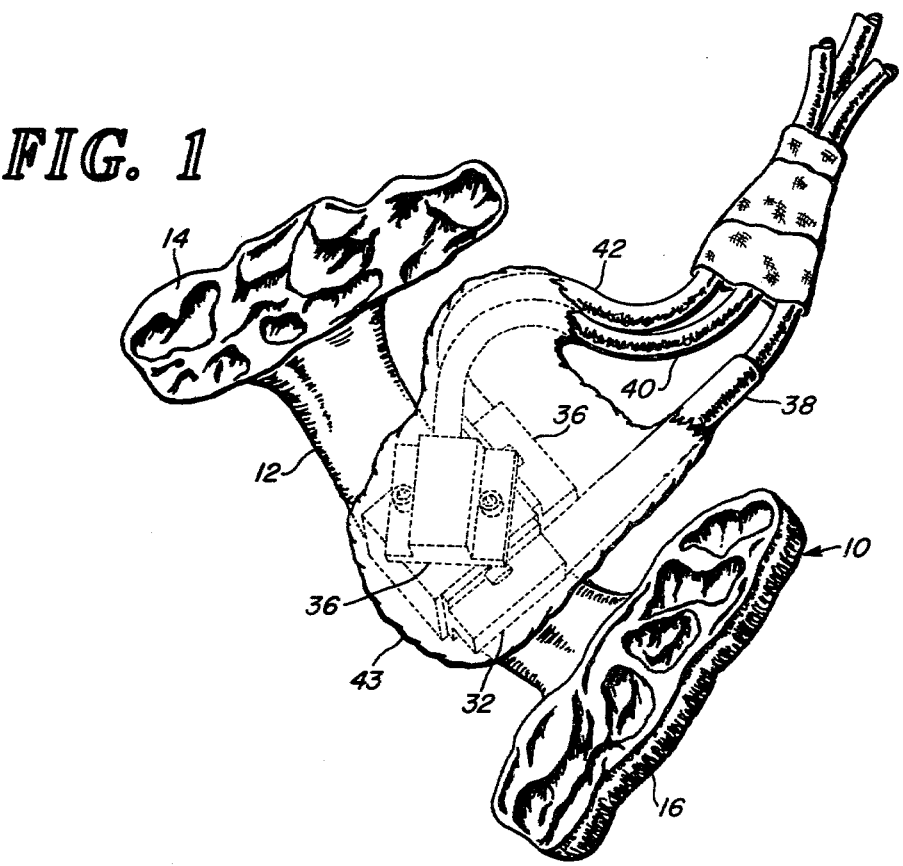
FIG. 1 is an isometric view of an accelerometer support mouthpiece according to the invention.

Reference is now made to FIG. 1 of drawing which shows a mouthpiece 10 including a support bridge member 12 and two teeth engaging members 14 and 16. The teeth engaging members 14 and 16 include metal clip members 20, 21, 22 and 23, shown in FIG. 2, for attaching the mouthpiece to the teeth of the test subject as illustrated in FIG. 3.

Figure 2:
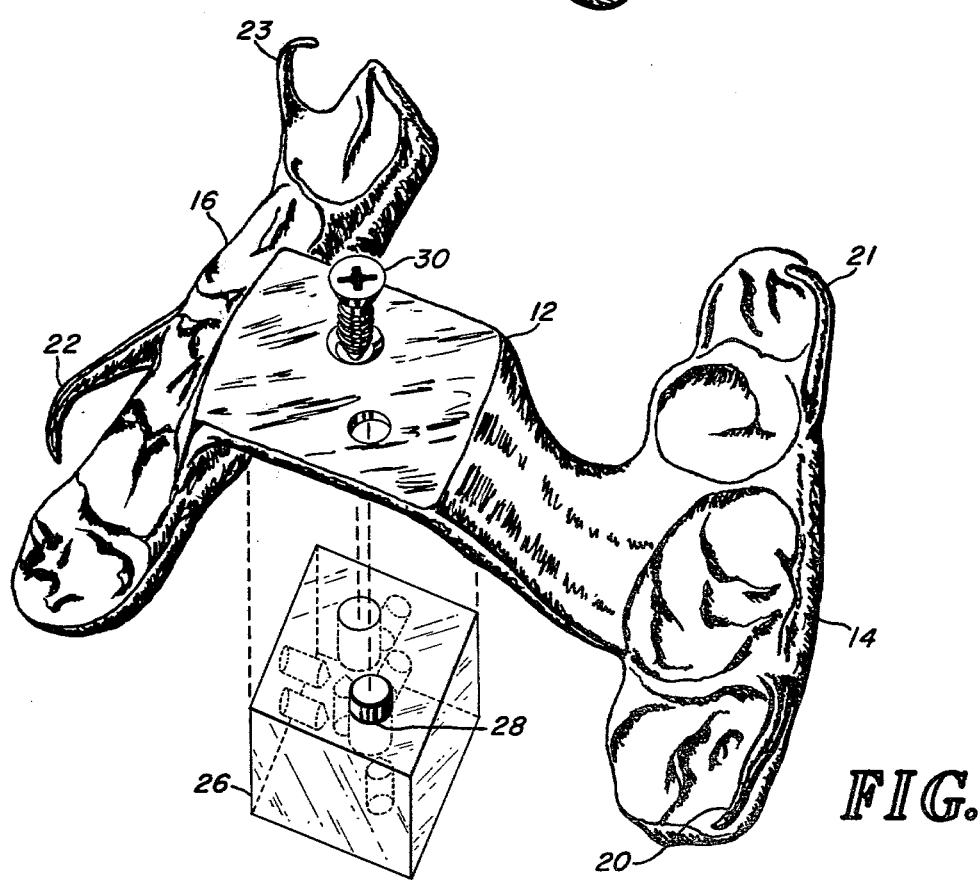
FIG. 2 is an expanded view of the mouthpiece support and accelerometer support block of the device of FIG. 1.
Figure 3:
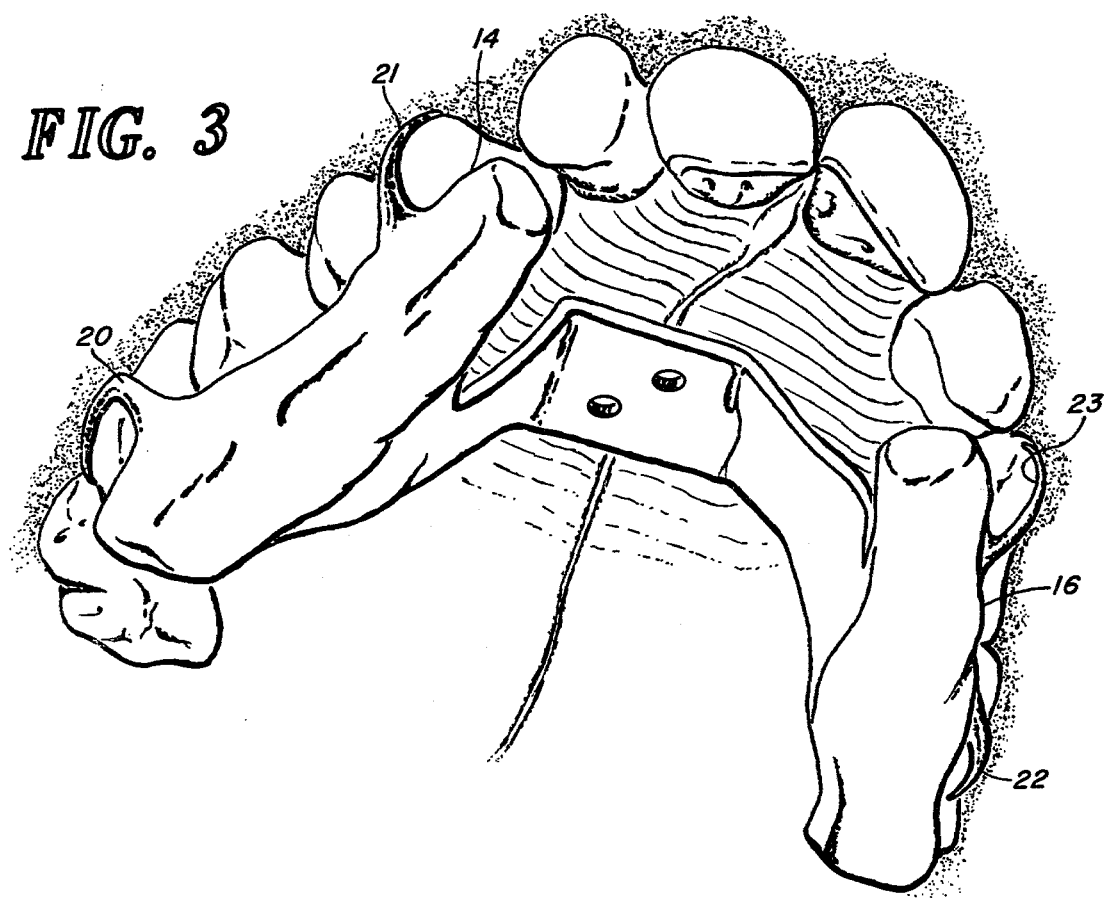
FIG. 3 is a partially schematic view of the device of FIG. 1 secured to the teeth, as in a test subject.

An accelerometer mounting block 26 is positioned on and secured to the bridge member 12 by means of a positioning pin 28 and a screw 30, as shown in the expanded view in FIG. 2.

Figure 4:
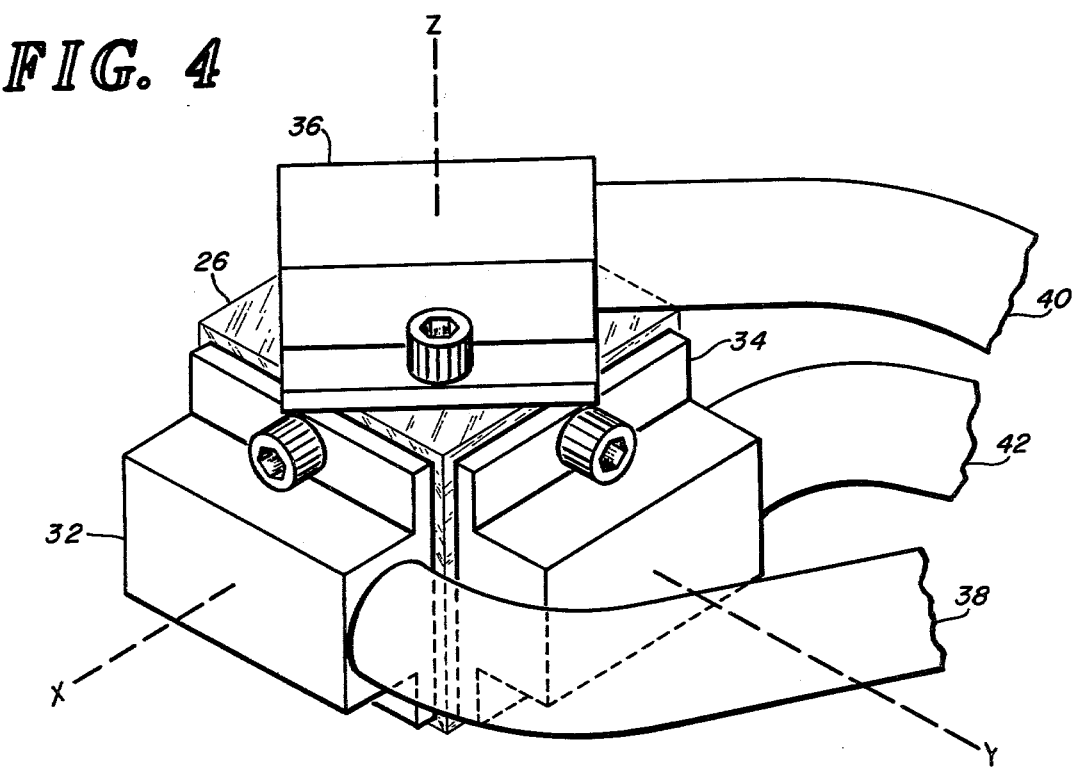
FIG. 4 shows the accelerometers and the support block for the device of FIG. 1.

Three accelerometers 32, 34 and 36 are secured to three nonopposing surfaces of mounting block 26 with their active axis along orthogonal axis X, Y and Z, respectively, as shown in FIG. 4. The mounting block, the accelerometers and the ends of accelerometer leads 38, 40 and 42 are coated with an electrical insulation material 43, as shown in FIG. 1.

Figure 5:
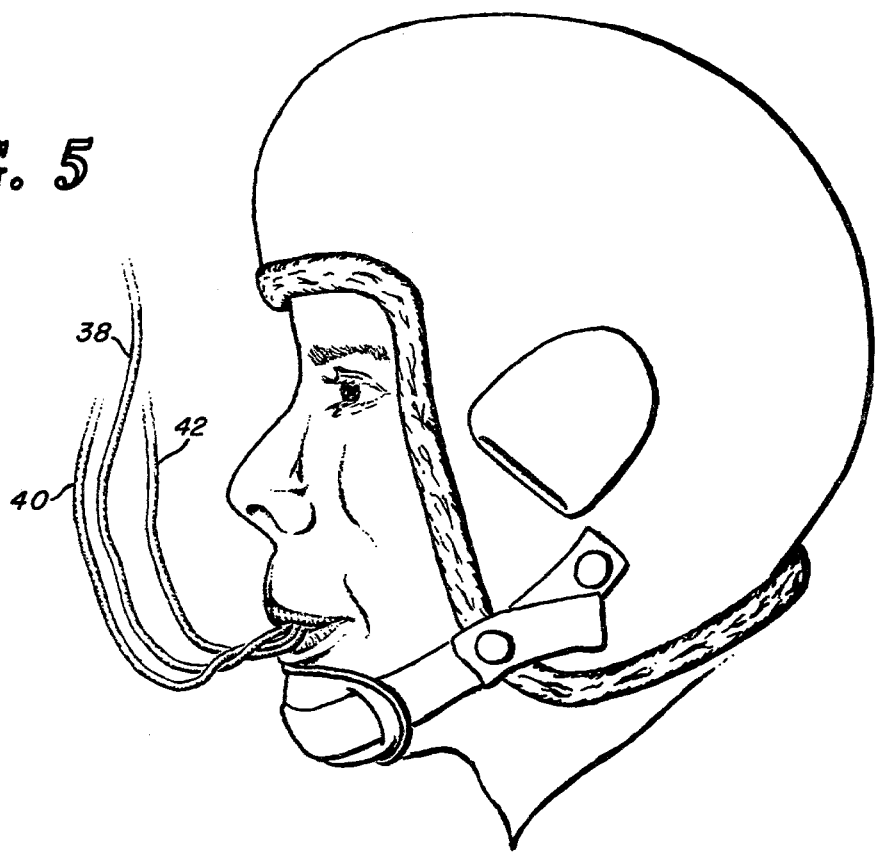
FIG. 5 shows the accelerometer leads of the device of FIG. 1 extending from the mouth of a test subject.
Figure 6:
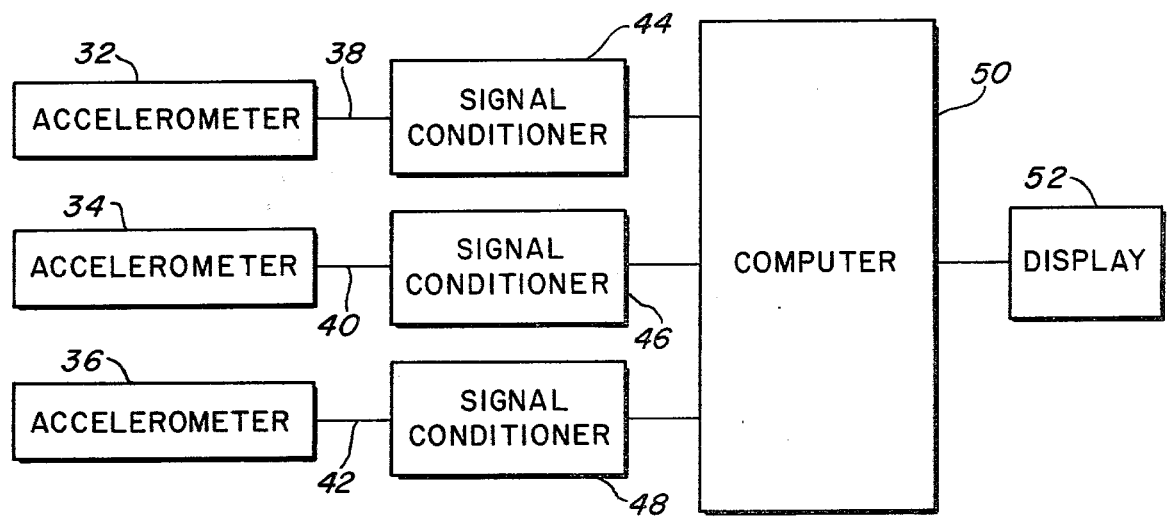
FIG. 6 is a block diagram of one utilization circuit for the device of FIG. 1.

The mouthpiece and accelerometer unit shown in FIG. 1 is secured to the upper teeth of a test subject with the accelerometer leads 38, 40 and 42 passing out between the teeth of the test subject, as illustrated in FIG. 5. A rubber mouthpiece, not shown, fits over the lower teeth of the test subject to provide protection for the lower teeth. The rubber mouthpiece and metal mouthpiece will space the teeth of the test subject to permit passage of the accelerometer leads between the teeth to signal conditioning circuits 44, 46 and 48 to computer 50 and display device 52, shown in FIG. 6.

In a device constructed, the mouthpiece 10 was made of a standard chromium-nickel alloy sold under the trade name Ticonium; however, any metal dental bridge material may be used. The mounting block used was made of a synthetic resin, such as plexiglass, and the electrical insulation material used was medical grade silicone elastic material.

In the operation of the device, the mouthpiece 10, with the accelerometers 32, 34 and 36, is attached to the upper teeth of a test subject. As the head of the test subject undergoes accelerations, either in a test apparatus or in actual flight conditions, the head accelerations, as measured by the accelerometers, are recorded or displayed. With the mouth mounted accelerometers, the flight helmet will not interfere with the accelerometers as in tests wherein the accelerometers are secured externally on the head of the test subject.

There is thus provided an apparatus for measuring head accelerations of a test subject which prevents relative movement between the accelerometers and the head of the test subject and which can provide reproducible results.

We claim:

1. An apparatus for measuring head accelerations of a test subject, comprising: a metal mouthpiece adapted to be secured to the upper teeth of the test subject; means, secured to said mouthpiece, supporting three accelerometers along three orthogonal axis; means, adapted to pass between the upper and lower teeth of the test subject, for transmitting signals from said accelerometers to at least one external signal processing circuit.

2. The device as recited in claim 1 wherein said means for supporting said accelerometers on said mouthpiece includes a synthetic mounting block removably secured to said mouthpiece; said accelerometers being mounted on three nonopposing surfaces of said mounting block.

3. The device as recited in claim 2 wherein said means for transmitting signals from said accelerometers to external signal processing circuits include leads connected to said accelerometers; means, coating said mounting block, said accelerometers and said leads for electrically insulating said leads and said accelerometers.

* * * * *

UNITED STATES PATENT AND TRADEMARK OFFICE
CERTIFICATE OF CORRECTION

PATENT NO. : 4,198,990

DATED : April 22, 1980

INVENTOR(S) : Aubin M. Higgins, James A. Fowler, Jr., Rober W. Mercer, and Gunter H. Kroh It is certified that error appears in the above—identified patent and that said Letters Patent are hereby corrected as shown below:

Col. 2, line 58, after "synthetic" insert -- resin --.

Signed and Sealed this

Twenty-sixth Day of August 1980

[SEAL]

Attest:

SIDNEY A. DIAMOND

Attesting Officer

Commissioner of Patents and Trademarks